US011464751B2

(12) United States Patent
Rubinstenn

(10) Patent No.: US 11,464,751 B2
(45) Date of Patent: Oct. 11, 2022

(54) USE OF FLUOROETHYLNORMEMANTINE FOR THE PREVENTION AND TREATMENT OF ANXIETY

(71) Applicant: REST THERAPEUTICS, MONTPELLIER (FR)

(72) Inventor: Gilles Rubinstenn, Paris (FR)

(73) Assignee: REST THERAPEUTICS, Montpellier (FR)

( * ) Notice: Subject to any disclaimer, the term of this patent is extended or adjusted under 35 U.S.C. 154(b) by 7 days.

(21) Appl. No.: 16/772,582

(22) PCT Filed: Dec. 17, 2018

(86) PCT No.: PCT/EP2018/085333
§ 371 (c)(1),
(2) Date: Jun. 12, 2020

(87) PCT Pub. No.: WO2019/115833
PCT Pub. Date: Jun. 20, 2019

(65) Prior Publication Data
US 2020/0383939 A1 Dec. 10, 2020

(30) Foreign Application Priority Data

Dec. 15, 2017 (FR) ...................... 1762290

(51) Int. Cl.
| | | |
|---|---|---|
| *A61K 31/13* | (2006.01) | |
| *A61P 25/22* | (2006.01) | |
| *A61K 31/14* | (2006.01) | |
| *A61K 45/06* | (2006.01) | |

(52) U.S. Cl.
CPC .............. *A61K 31/13* (2013.01); *A61K 31/14* (2013.01); *A61P 25/22* (2018.01); *A61K 45/06* (2013.01)

(58) Field of Classification Search
CPC .......... A61K 31/13; A61K 31/14; A61P 25/22
See application file for complete search history.

(56) References Cited

U.S. PATENT DOCUMENTS

| | | | |
|---|---|---|---|
| 9,714,212 B2* | 7/2017 | Guerret ................. | C07C 211/38 |
| 2014/0057988 A1 | 2/2014 | Weg | |
| 2016/0030391 A1 | 2/2016 | Gallagher et al. | |
| 2016/0107982 A1 | 4/2016 | Guerret et al. | |

FOREIGN PATENT DOCUMENTS

| | | |
|---|---|---|
| EP | 0216555 A2 | 4/1987 |
| EP | 2905021 A1 | 8/2015 |
| JP | 2007-148435 A | 6/2007 |
| WO | WO 2009/006548 A2 | 1/2009 |
| WO | WO 2014/191424 A1 | 12/2014 |

OTHER PUBLICATIONS

Schwartz et al., "Memantine as an Augmentation Therapy for Anxiety Disorders", Case Reports in Psychiatry, vol. 2012, Article ID. 749796, pp. 1-3 (Feb. 2012).*
Adamec et al., "NMDA Receptors Mediate Lasting Increases in Anxiety-Like Behavior Produced by the Stress of Predator Exposure-Implications for Anxiety Associated with Posttraumatic Stress Disorder," Physiology & Behavior, vol. 65, Nos. 4/5, 1999, pp. 723-737.
Bandelow et al., "Guidelines for the Pharmacological Treatment of Anxiety Disorders, Obsessive-Compulsive Disorder and Post-traumatic Stress Disorder in Primary Care," International Journal of Psychiatry in Clinical Practice, vol. 16, 2012, pp. 77-84.
Borsini et al., "Is the Forced Swimming Test a Suitable Model for Revealing Antidepressant Activity?," Psychopharmacology, vol. 94, 1988, pp. 147-160.
Bourin et al., "The Mouse Light/ Dark Box Test," European Journal of Pharmacology, vol. 463, 2003, pp. 55-65.
Cahill et al., "β-Adrenergic Activation and Memory for Emotional Events," Nature, vol. 371, Oct. 20, 1994, pp. 702-704.
Carlier et al., "Antidepressant in the Treatment of Posttraumatic Stress Disorder," Annales Médico-Psychologiques. vol. 166, 2008 (Oct. 1, 2008), pp. 747-754, with an English abstract.
Famularo et al., "Propranolol Treatment for Childhood Post-traumatic Stress Disorder, Acute Type," AJDC, vol. 142, Nov. 1988, pp. 1244-1247.
French Preliminary Search Report, dated Aug. 1, 2018, for French Application No. 1762290.
International Search Report and Written Opinion of the International Searching Authority (forms PCT/ISA/210, PCT/ISA/237 and PCT/ISA/220), dated Feb. 20. 2019, for International Application No. PCT/EP2018/085333.
Mcgowan et al., "Prophylactic Ketamine Attenuates Learned Fear," Neuropsychopharmacology, 2017 (preview online Jan. 27, 2017), pp. 1-13.
Prut et al., "The Open Field as a Paradigm to Measure the Effects of Drugs on Anxiety-Like Behaviors: A Review," European Journal of Pharmacology, vol. 463, 2003, pp. 3-33.
Roy, "S6UE1: Psychobiology of Emotions and Addictions," Animal Models of Anxiety Disorders. Lessons Vincent Roy, http://psychobiologierouen.free.fr/?page_id=40, 2013, 1 page, with an English translation.
Sani et al., "The Role of Memantine in the Treatment of Psychiatric Disorders Other Than the Dementias, A Review of Current Preciinical and Clinical Evidence," CNS Drugs vol. 26, No. 8, 2012, pp. 663-690.
Shalev et al., "Prospective Study of Posttraumatic Stress Disorder and Depression Following Trauma," Am Psychiatry, vol. 155, No. 5, May 1998, pp. 630-637.
Swerdlow et al., "The Effects of Memantine on Prepulse Inhibition," Neuropsychopharmacology, vol. 34, 2009 (Published online Feb. 25, 2009), pp. 1854-1864.
Teigell-Webb, "Study of the Intrinsic Neurotoxicity of an Antagonist of NMDA Receptors: The Gacyclidin, 'in-vitro' and 'in-vivo' study," Dissertation, École Pratique des Hautes Études (EPHE), Apr. 20, 2006, pp. 1-24.
United States Securities and Exchange Commission, Form 8-K, Tonix Pharmaceuticals Holding Corp., Dec. 19, 2016, pp. 1-35 (total 42 pages).

(Continued)

*Primary Examiner* — Kevin E Weddington
(74) *Attorney, Agent, or Firm* — Pearne & Gordon LLP

(57) ABSTRACT

The present invention relates to fluoroethylnormemantine or one of the salts thereof for the treatment of anxiety and, more particularly, post-traumatic stress conditions, either alone or in combination with chemical antidepressant treatments or cognitive and behavioral techniques.

12 Claims, 1 Drawing Sheet

(56) References Cited

OTHER PUBLICATIONS

Womble, "Effects of Ketamine on Major Depressive Disorder in a Patient with Posttraumatic Stress Disorder," AANA Journal, vol. 81, No. 2, Apr. 2013, pp. 118-119.

Zovkic et al., Epigenetic Mechanisms in Learned Fear: Implications for PTSD/Neuropsychopharmacology Reviews, vol. 38, 2013 (published online Jun. 13, 2012), pp. 77-93.

Adamantane, Wikipedia, https://en.wikipedia.org/wiki/Adamantane (last accessed May 5, 2022).

Amantadine, Wikipedia, https://en.wikipedia.org/wiki/Amantadine (last accessed May 5, 2022).

"Rimantadine," Wikipedia, https://en.wikipedia.org/wiki/Rimantadine (last accessed May 5, 2022).

Limapichat, et al., "Key Binding Interactions for Memantine in the NMDA Receptor," ACS Chem. Neurosci. Feb. 20, 2013; 4(2):255-260, 255 (e-publication available on Dec. 7, 2012).

NDMA receptor, Wikipedia, https://en.wikipedia.org/wiki/NMDA_receptor (last accessed May 4, 2022).

* cited by examiner

FIGURE 1

| Treatment condition | Fear conditioning phase (FC) 3 sound-electroshock pairs, 1mA, 1s | Extinction phase (Ext) 24 sounds, 35 s | Stab phase (Stab) 3 sounds |
|---|---|---|---|
| Protective effect | Injection 30min before FC: FENM (5,10,20,mg/kg), propanolol, control solution | | |
| Early treatment | | Injection 30min before Ext: FENM (5,10,20,mg/kg), propanolol, control solution | |
| Late treatment | | | Injection 30min before Stab: FENM (5,10,20,mg/kg), propanolol, control solution |

TABLE 7

USE OF FLUOROETHYLNORMEMANTINE FOR THE PREVENTION AND TREATMENT OF ANXIETY

The present invention relates to the discovery of the use of a pharmaceutical component in the treatment of disorders related to anxiety and depression.

DESCRIPTION OF THE PRIOR ART

A number of molecules have been developed to treat anxiety and depression-related anxiety. However, these molecules have many shortcomings, in particular substantial side effects, either causing a relative increase in drowsiness, or even leading to schizophrenic psychotic states, or requiring a significant amount of treatment time (several days or even weeks) before the therapeutic effect appears, with a risk of an anxiogenic effect during the treatment period.

Anxiety

Human anxiety is a feeling of worry, insecurity, physical or mental disorder or an expectation of indeterminate danger. Two types of anxiety are also distinguished: state anxiety and trait anxiety. State anxiety is a "normal" anxiety related to a specific situation in which the subject finds himself. Trait anxiety of is a "pathological" anxiety, constitutive of a subject. It is permanent and independent of a particular situation.

Depression

Depression is characterized by so-called depressive episodes in which the patient experiences a lowering of mood, reduced energy and decreased activity. During depression, there is also an altered ability to experience pleasure, a loss of interest, and a rapid decrease in the ability to concentrate. There is also significant fatigue even after minimal effort, sleep disturbances, etc. Patients frequently experience a decrease in self-esteem, feelings of guilt and low self-esteem, which can be as extreme as a death wish and the development of suicidal thoughts. Depending on the number and the severity of symptoms, three degrees of severity of depression are defined: mild, moderate and severe.

Several mental disorders are listed in the Classification of Diseases (ICD-10) proposed by the World Health Organization (WHO) that associate anxiety and depression:

Phobic Anxiety Disorders: F40

The subject presents anxiety symptoms that are triggered exclusively or essentially by one or more specific and harmless situations. As a result, the patient will try to avoid these situations or endure them with apprehension. This phobic anxiety is often associated with depression.

Mixed Anxiety and Depressive Disorder: F41.2

In this case, the subject presents both anxiety and depressive symptoms without a clear predominance of either and without the intensity of either warranting a separate diagnosis.

Obsessive-Compulsive Disorder (OCD): F42

This disorder is characterized by recurrent obsessive thoughts or compulsive behaviors. Obsessive thoughts repeatedly and stereotypically intrude into the subject's consciousness, even when the subject is trying to avoid them. Compulsive behaviors are also repetitive stereotyped activities in which the subject feels no direct pleasure but cannot help but perform them. Their purpose is to prevent the occurrence of an objectively unlikely event involving unhappiness for the subject. The subject usually recognizes the absurdity of his or her behavior and makes repeated efforts to stop it. This disorder is almost always accompanied by anxiety and depression.

Post-Traumatic Stress Disorder (PTSD): F43.1

Post-traumatic stress disorder develops following exposure (direct or indirect) of the subject to a traumatic event in a context of death, death threats, serious injury or sexual assault, etc. By definition threatening and resulting in an intense fear reaction, this 'traumatic' event represents a situation of extreme stress. It results in a set of specific symptoms and behaviors. For example: flashbacks (repetitive and invasive memories of the event, nightmares, etc.), avoidance behaviors (avoidance of memories, thoughts, people, situations, etc. recalling the traumatic event), cognitive and emotional changes (tendency to blame oneself, persistent negative emotions, etc.) and finally hyperactivation of the nervous system (hypervigilance, difficulty sleeping, etc.). People who suffer from this syndrome also often develop deep depression or suicidal ideation (Shalev, Am. J. Psychiatry 155,5, p 630-637, May 1998). This post-traumatic stress disorder phenomenon is linked to a profound distortion of the memory encoding of events. The memory is stored in the long term but in a biased way, with amnesia for certain aspects and hypermnesia for other details harassing the subject.

There is therefore a real need for new solutions to effectively address anxiety disorders, whether or not coupled with depression.

Treatment of Disorders Combining Anxiety and Depression

Conventional treatments for anxiety, whether or not associated with depression, include behavioral therapy, lifestyle change and pharmaceutical therapy. However, a large number of the drugs used to treat these disorders are known to have either embarrassing side effects or are responsible for addiction or dependence (Thesis A. Dubois 2015 Université de Bordeaux). Most of the therapeutic solutions currently used to treat anxiety-related disorders, as well as some of their side effects, can be found in the following review: Guidelines for the pharmacological treatment of anxiety disorders, obsessive-compulsive disorder and posttraumatic stress disorder in primary care, B. Bandelow, International Journal of Psychiatry in Clinical Practice, 2012; 16: 77-84.

Among the earliest substances used, for example, were barbital derivatives, known as barbiturates, which were widely used in the 1950s but were at high risk of addiction or intolerance.

Other drugs to treat anxiety and depression were then developed, in particular benzodiazepines, the leader of which is diazepam (Valium®, etc.). These molecules, initially presented as effective and relatively well-tolerated, have been and are still widely prescribed, particularly in France and the United States. Benzodiazepines have the ability to bind to a cell receptor, normally reserved for GABA (γ-aminobutyric acid). This natural chemical compound is the main inhibitor of the central nervous system. By binding to the cell receptor, benzodiazepines increase the affinity of these receptors for GABA, thus increasing its potency tenfold. However, it has been shown that there is a significant drug-dependence to these molecules as well as other unwanted effects (impaired cognitive function, schizophrenic disorders, drowsiness, withdrawal syndrome and rebound phenomena, etc.) and alternatives have therefore been sought. Furthermore, benzodiazepines have not been found effective in the treatment of OCD and other disorders combining anxiety and depression.

Another class of anti-anxiety and anti-depression molecules was then developed, based on the action of another neurotransmitter: serotonin (5-hydroxytryptamine or 5-HT). It is a neurotransmitter released when information is exchanged between an emitter neuron and a receptor neuron. Selective serotonin reuptake inhibitors, or SSRIs, include fluoxetine (Prozac®) and vortioxetine (Trintellix®, Brintellix®). Some of the information between the sending and receiving neuron is lost because the neurotransmitter is re-captured by the sending neuron and not available to the receiving neuron. SSRIs work by preventing the transmitter neuron from re-capturing serotonin, increasing the likelihood that serotonin will be recognized by the receiving neuron, thereby increasing the stimulation of that neuron. To exploit this property, many SSRI molecules have been developed (see for example patent EP0216555A2). The results against anxiety and depression have been very promising, but here again side effects have been observed (in particular behavioral disinhibition, etc.). Moreover, evidence of the effectiveness of SSRIs in reducing the severity of PTSD symptoms has been provided, particularly in the case of paroxetine and sertraline (P Cartier, Annales médico-psychologiques 166, 2008, 747-754). However, here again, side effects have appeared (paranoia, serotonin syndrome, etc.) as well as a certain number of intolerances or ineffectiveness justifying the need to combine SSRIs with other antidepressants (mood stabilizer, etc.).

Another neurotransmitter, glutamate, is also the subject of intensive research to develop new drugs. It is now accepted that glutamate activates several types of receptors (M. Teigell-Webb, EPHP dissertation): glutamate acts on three ionotropic receptors, characterized and named by the name of their most selective agonist: N-methyl-D-aspartate (NMDA), kainate (KA), and a-amino-3-hydroxy-5-methyl-4-isoxazolepropionate (AMPA) receptors. Study of the NMDA receptor developed more rapidly as research showed that NMDA receptors were involved in interesting aspects of brain function. NMDA receptors play a wide variety of physiological roles: neuronal differentiation, formation of synaptic connections during development, synaptic plasticity in adults. In particular, it has been shown in adults that the NMDA receptor is involved in learning and short-term memory; in certain regions of the hippocampus, it helps strengthen synaptic efficiency (or long-term potentiation) which would serve as a medium for information storage. Finally, the involvement of the NMDA receptor in the increase in anxious behavior following exposure to stress (R. E. Adamec et al., Physiology & Behavior, Vol. 65, Nos. 4/5, pp. 723-737, 1999) makes it a prime target for the development of treatment for PTSD. Note that the novelty of the glutamate receptor is that, unlike other ligand-activated receptor channels, there is a twin dependence on agonist (and co-agonist) binding and membrane potential for this receptor. At the glutamate site, competitive agonists and antagonists bind. Non-competitive NMDA receptor antagonists are molecules capable of binding to a different regulatory site than glutamate. In the case of the treatment of anxiety, for example, NMDA receptor-inhibiting peptides have been developed (Patent EP2175873).

In addition, so-called "channel blockers" are agents that bind within the channel associated with the NMDA receptor when the NMDA receptor is in the "open" position (depolarized cell and glutamate bound). Among the best known "channel blockers" are ketamine, memantine, etc. The latter molecule has already shown neuroprotective effects. For example, it is already used for the treatment of Alzheimer's disease, but it has also been tested to treat behavioral disorders in children (autism), for example in patent US2010081723A1.

Also note that non-competitive antagonists binding to the phencyclidine (PCP) site of the NMDA receptor such as ketamine, dizocilpine, memantine have also been tested for anxiety related to post-traumatic stress (Arthur L. Womble, AANA Journal April 2013 Vol. 81, No. 2.). With regard to ketamine and dizocilpine, the positive results of these studies are strongly overshadowed by the side effects (hallucinations, flashbacks, paranoia, etc.). It should be noted that ketamine strongly inhibits sensory filtering.

The development of ketamine is nevertheless being pursued by several teams who have demonstrated an interesting prophylactic effect when the molecule is injected in a single injection, 1 week before fear conditioning in rodents (C. Denny et al., in Neuropsychopharmacology (2017), 1-13), resulting in a significant reduction in tetany during the stabilization phase. Nevertheless, the effect is only visible at high doses for this model (30 mg/kg) and is not reproduced if treatment is concomitant (or just before) conditioning or if protective treatment is done too early (1 month in advance).

US 2014/057988 A1 also proposes the use of ketamine as an NMDA receptor antagonist for the inhibition, amelioration or treatment of the development of mild anxiety, where mild anxiety is defined in this document as a feeling of discomfort or apprehension. This document discusses and cites the use of memantine in the treatment of dementia, but memantine does not have an anxiolytic effect and has schizophrenia-like adverse side effects.

WO 2014/191424 describes the use of memantine derivatives, in particular 2-fluoroethylnormemantine, in the treatment of neurodegenerative diseases such as Alzheimer's or Parkinson's disease.

Memantine has also been used to treat anxiety disorders, whether or not associated with depression, such as PTSD and obsessive compulsive disorder (G. Sani, review article CNS Drugs 2012; 26 (8): 663-690). In general, the action of memantine is positive when used in combination (augmentation therapy) with other molecules. Its efficacy is much weaker and controversial when used as monotherapy. For example, to treat OCD, memantine has been combined with SSRIs such as fluoxetine or citalopram, or with other tricyclic antidepressants such as clomipramine. In general, the use of memantine as adjunctive therapy is well tolerated at low daily doses (less than about 15 mg/day). However, side effects such as dysphoric state, drowsiness, nausea have been observed when too high doses were administered. The results of use in animal models of PTSD have not been convincing, but in a few case studies of human PTSD, memantine used as an additive treatment appeared to improve the symptoms of these patients. In any case, memantine used alone is not able to reduce or treat anxiety, whether mild or severe, whether or not it is associated with depression. Other uses in combination with other molecules include the use of memantine in combination with inhibitors of the synaptic vesicle glycoprotein SV2A (US patent 2016030391A1) and the memantine/melatonin combination (patent EP 2905021 A1).

Moreover, although it appears to have few side effects and is well tolerated, memantine appears to have unintended hyper-tranquilizing effects (drowsiness, fatigue, apathy, etc.), and also leads at high dose to an increase in dizziness (N R Swerdlow, Neuropsychopharma., 2009, 34, 1854-1864) and a rebound effect that has been reported by patients on internet forums. Furthermore, it is well known that memantine, especially at high doses, or the fact that it is not anxiolytic, is capable of inducing schizophrenia-type side effects.

Finally, in the case of NMDA receptors, it appears that the different antagonists do not act in a single way, so that the advantages and disadvantages of one antagonist are not necessarily the same for another antagonist, even if the structures are similar.

For the secondary treatment of PTSD, a final class of molecules has been proposed: catecholaminergic agents (F. Ducrocq, L'Encéphale, 2005; 31: 212-26). They have been used in pharmacological interventions aimed at directly suppressing noradrenergic hyperreactivity, and have been studied through open and double-blind trials on small numbers of patients. These agents include clonidine, guanfacine, prazosin and propranolol. Of these molecules, propranolol has been the subject of the most conclusive work to date. This non-selective β-adrenergic blocker was thus theorized as early as 1994 as capable of reducing the phenomena of consolidation of emotional memory in the immediate aftermath of a traumatic event (Cahill L., Nature 1994; 371:702-4.). Several earlier, Famularo et al. had tested the molecule in the disorder constituted in children by constructing a study based on a B-A-B (off-on-off) design of 3 phases of 4 weeks of treatment interspersed with phases of 2 weeks of withdrawal. In this study, 8 of the 11 children enrolled showed a significant improvement in their PTSD symptoms (repetition and neurovegetative hyper-reactivity) during the treatment phases, but this improvement disappeared during withdrawal (Famularo R, Am J Dis Child 1988; 142:1244-7.). This last element considerably limits the interest of propranolol beyond the accompaniment of cognitive therapies for PTSD.

The lack of an efficient solution for the treatment of PTSD is also demonstrated by the situation related to prescriptions. A recent study (Tonix Pharmaceuticals Holding Corp. (TNXP) FORM 8-K | Current report Dec. 19, 2016. UNITED STATES SECURITIES AND EXCHANGE COMMISSION Washington, D.C. 20549 Pursuant to Section 13 or 15(d) of the Securities Exchange Act of 1934) showed that in the United States, while only the SSRI class is approved by the FDA for the treatment of PTSD, the first class of drugs prescribed is the benzodiazepine class for 55% of patients, compared to 53% for SSRIs.

BRIEF DESCRIPTION OF DRAWINGS

FIG. 1 illustrates table 7 referred to in the specification, depicting a fear conditioning test administered to rats according to Example 5 as hereafter described.

DETAILED DESCRIPTION

Faced with the need for efficient solutions for the treatment of PTSD, the applicant therefore imagined using a molecule derived structurally from memantine but with a very different dipole moment generated by the introduction of a fluorine atom to treat anxiety, whether or not associated with depression. In the specific case of PTSD, the applicant surprisingly discovered that the molecule could act both as protection, i.e. by administration concomitantly with the traumatic event, and for subsequent or even delayed treatment. The applicant further determined that the molecule did not exhibit the many undesirable side effects of the prior art or proposed treatments under investigation.

It is thus a first object of the invention to propose a compound of formula (I) or a pharmaceutically acceptable salt thereof

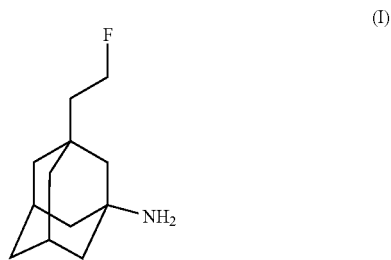 [SMILES: NC12CC3CC(C1)CC(CCF)(C3)C2]

(I)

for use in the treatment or prevention of an anxiety disorder in a patient. The compound (I) for use according to the invention is characterized in that it is devoid of schizophrenia-inducing effect.

The term "devoid of schizophrenia-inducing effect" means that compound (I) does not induce—at doses for the treatment or prevention of an anxiety disorder—schizophrenia or associated symptoms such as schizophrenic delusions, paranoid delusions, hallucinations, attention deficit disorder, withdrawal, incoherence or disorganization.

In a second embodiment, the invention relates to a compound for use according to the first embodiment, characterized in that the pharmaceutically acceptable salt corresponds to the formula (II)

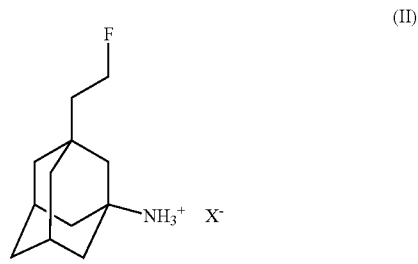

(II)

wherein, X$^-$denotes a counter-anion selected from the group consisting of chloride, bromide, iodide, acetate, methane sulfonate, benzene sulfonate, camphosulfonate, tartrate, dibenzoate, ascorbate, fumarate, citrate, phosphate, salicylate, oxalate, bromohydrate and tosylate ions.

It is also a third object of the invention to propose a compound for use according to one of embodiments 1 or 2, characterized in that the anxiety disorder is associated with depression.

The compound is characterized in that it is devoid of schizophrenia-inducing effect.

It is the object of a fourth embodiment of the invention to provide a compound for use according to one of embodiments 1 or 2, characterized in that the anxiety disorder observed is associated with insomnia.

The invention further relates, in a fifth embodiment, to a compound for use according to one of embodiments 1 to 4, characterized in that the anxiety disorder is selected from the group consisting of post-traumatic stress disorder (PTSD), specific phobia, social phobia, generalized anxiety disorder, panic disorder with or without agoraphobia and obsessive compulsive disorder.

The compound is characterized in that it is devoid of schizophrenia-inducing effect.

In a sixth embodiment, the invention further relates to a compound for use according to one of embodiments 1 to 5, characterized in that it is used for a treatment to prevent the appearance of anxiety disorders related to post-traumatic stress.

The compound is characterized in that it is devoid of schizophrenia-inducing effect.

The treatment of PTSD-related anxiety disorders includes in particular the treatment of any combination of at least one of the DSM 5 criteria for PTSD selected from the group consisting of: flashbacks, avoidance, negative cognition and mood, and hyper-responsiveness.

Flashbacks refers particularly to the associated nightmares. Negative cognition and mood refers to depressive states.

According to the embodiments of the invention, compound (I) or (II) can be administered in doses comprising 1 mg to 1000 mg of compound (I) or (II), for example 5 to 250 mg, for example 5 to 100 mg and preferably 5 to 30 mg of compound (I) or (II). The doses in question can be administered, for example, 1 to 4 times a day, for example 1 time, for example two times, in particular 3 times, or even 4 times.

According to a particular embodiment, the compound (I) for use according to the invention is characterized in that it is devoid of schizophrenia-inducing effect. In a seventh embodiment, the invention relates to a compound for use according to embodiment 6, characterized in that the treatment comprises the administration of the compound concomitantly with the traumatic event causing post-traumatic stress.

An eighth embodiment of the invention further relates to a compound for use according to embodiment 6, characterized in that the treatment comprises administering the compound for 4 to 18 weeks following the traumatic event causing post-traumatic stress.

The compound can be administered for 4, 5, 6, 7, 8, 9, 10, 11, 12, 13, 14, 15, 16, 17 or 18 weeks.

It is a ninth embodiment to provide a compound for use according to one of embodiments 1 to 5, characterized in that the anxiety disorder is related to post-traumatic stress, in particular established post-traumatic stress.

The compound is characterized in that it is devoid of schizophrenia-inducing effect.

In a tenth embodiment, the invention relates to a compound for use according to embodiment 9, characterized in that the patient presenting an anxiety disorder follows an antidepressant therapy selected from behavioral therapies and pharmacological antidepressant treatments.

Pharmacological antidepressant treatment means the administration of at least one chemical molecule known for the treatment of depression. These include serotonin reuptake inhibitors such as fluoxetine, vortioxetine, fluvoxamine, sertraline, paroxetine, citalopram, escitalopram, duloxetine, milnacipran, venlafaxine, indalpine, zimelidine, dapoxetine.

In an eleventh embodiment, the invention relates to a compound for use according to embodiment 10, characterized in that the patient is undergoing propanolol-based treatment.

According to a twelfth embodiment, the invention relates to a compound for use according to one of embodiments 1 to 11, characterized in that the anxiety disorder is accompanied by acute anxiety attacks and episodes.

The invention further relates, in a thirteenth embodiment, to a combination product, in particular for simultaneous, separate or sequential use, comprising the following components: a component (A) comprising a compound of formula (I) or a pharmaceutically acceptable salt thereof and at least one pharmaceutically acceptable excipient

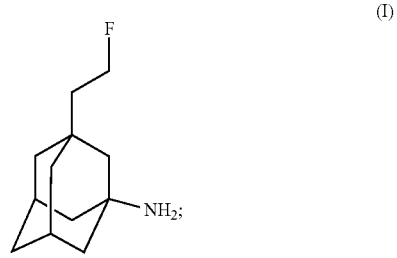

a component (B) comprising propranolol and at least one pharmaceutically acceptable excipient.

According to a particular embodiment of the product according to the invention, it is characterized in that it is devoid of schizophrenia-inducing effect.

It is a fourteenth embodiment of the invention to provide a combination product comprising the following components: a component (A) comprising a compound of formula (I) or a pharmaceutically acceptable salt thereof

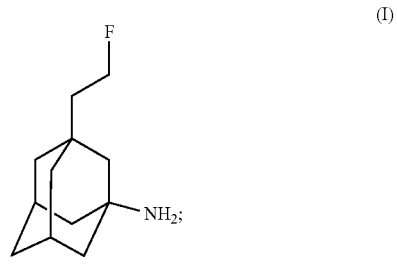 [SMILES: NC12CC3CC(C1)CC(CCF)(C3)C2]

a component (C) comprising an antidepressant, in particular one of the serotonin reuptake inhibitors described in embodiment 10; wherein each of components (A) and (C) is formulated with at least one pharmaceutically acceptable excipient.

According to a particular embodiment of the product according to the invention, it is characterized in that it is devoid of schizophrenia-inducing effect.

In a fifteenth embodiment, the invention further relates to a product according to embodiment 13, further comprising in combination, a component (D) comprising ketamine formulated with a pharmaceutically acceptable excipient.

In a sixteenth embodiment, the invention further relates to a product according to embodiment 14, further comprising in combination, a component (D) comprising ketamine formulated with a pharmaceutically acceptable excipient.

In a seventeenth embodiment, the invention further relates to a product according to embodiment 13, in which components (A) and (B) are adapted for simultaneous, separate or sequential administration.

In an eighteenth embodiment, the invention relates to a product according to embodiment 14, in which components (A) and (C) are adapted for simultaneous, separate or sequential administration.

In a nineteenth embodiment, the invention relates to a product according to embodiment 15, in which components (A), (B) and (D) are adapted for simultaneous, separate or sequential administration.

According to a twentieth embodiment, the invention relates to a product according to embodiment 16, in which components (A), (C) and (D) are adapted for simultaneous, separate or sequential administration.

In a twenty-first embodiment, the invention relates to a product according to one of embodiments 13 to 20, for use in the prevention or treatment of an anxiety disorder in a patient.

According to a twenty-second embodiment, the invention relates to a product for use according to embodiment 21, characterized in that the patient is undergoing cognitive-behavioral therapy.

According to a twenty-third embodiment, the invention further relates to a product for use according to embodiment 22, characterized in that the treatment of the anxiety disorder is subsequent to cognitive-behavioral therapy.

In a twenty-fourth embodiment, the invention relates to a product according to one of embodiments 13 or 17, for use in the prevention or treatment of an anxiety disorder in a patient, said patient having suffered repeated abuse, in particular during childhood.

According to a twenty-fifth embodiment, the invention provides a product for use according to embodiment 24, characterized in that said patient is undergoing cognitive-behavioral therapy.

According to a twenty-sixth embodiment, the invention further relates to a product for use according to embodiment 25, characterized in that components (A) and (B) are used separately in time and after cognitive-behavioral therapy.

Indeed, the applicant has recently discovered a polarized derivative of memantine, 2-fluoroethylnormemantine (FENM) (see Formula I) which has an improved affinity for NMDA receptors (patent WO2014191424A1).

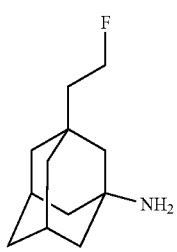

(I)

The molecule (I) can be in equilibrium with a protonated form of formula (II), wherein X⁻ denotes a counter-anion derived from the biological medium or chosen from chloride, bromide, iodide, acetate, methane sulfonate, benzene sulfonate, camphosulfonate, tartrate, dibenzoate, ascorbate, fumarate, citrate, phosphate, salicylate, oxalate, hydrobromide, tosylate ions. The product of formula (II) is therefore a pharmaceutically acceptable salt of the product of formula (I).

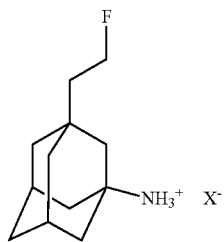

(II)

Note for example a particularly preferred acceptable pharmaceutical salt of fluoroethylnormemantine whose counter-anion is a chloride ion, i.e. FENM-HCl.

Investigative tests conducted during the development of NMDA as a biomarker showed that this molecule binds efficiently to the PCP (phencyclidine) site of the NMDA receptor when the channel of the NMDA receptor is in the "open" state, thus preventing in particular an excessive influx of $Ca^{2+}$ into the cell. Interestingly, this enhanced affinity is not due to a strong binding to the NMDA receptor, but to the high specificity of the molecule for the areas of the brain where the receptor is located, as well as its prolonged residence time in these areas. In fact, the existing correlation between NMDA and monoclonal antibodies demonstrating the efficiency of bio-labelling is lost when ketamine is injected. These preliminary examinations have also shown a rapid crossing of the blood/brain barrier.

Surprisingly, the applicant demonstrated that compound (I) (or a salt thereof, particularly FENM-HCl) can be used for the treatment of anxiety, whether or not associated with depression. In the specific case of PTSD, the applicant surprisingly discovered that compound (I) or a pharmaceutically acceptable salt thereof could act both in a protective manner, that is to say, by being administered at the same time as the traumatic event, and during subsequent or even delayed treatment. The applicant further determined that the molecule did not exhibit the many undesirable side effects of the prior art or proposed treatments under investigation.

The applicant also demonstrated an anxiolytic activity of the product (I) described here (light-dark box test and light gradient). Conversely, it was demonstrated under the same conditions that memantine has no anxiolytic activity.

The product (I) described here has a very significant anxiolytic activity, and its affinity with the NMDA receptor (measured in Ki) is of the same order of magnitude as that of memantine.

In the light-dark box test based on rodents' innate aversion to light, the increase in time spent in the lighted compartment is considered to reflect a lower level of anxiety; which is found for rodents treated with product (I) according to the invention. No effect is found for memantine for which it is therefore concluded and confirmed that it has no anxiolytic effect.

In addition, the inventors also demonstrated through a sensory filtering test that, unlike memantine, the product (I) does not induce any schizophrenia-inducing effect.

This is a key feature of the product (I), namely to treat anxiety, whether or not associated with depression, while not inducing a schizophrenia-inducing effect.

In the context of the present invention, the expression "administration concomitantly with the traumatic event" means that compound (I) is administered within a time window ranging from 48 hours before the traumatic event to 72 hours after the traumatic event. This "administration concomitantly with the traumatic event" can also be between 48 hours before and 48 hours after the traumatic event, or 48 hours before and 24 hours after the traumatic event, or 24 hours before and 24 hours after the traumatic event, or 24 hours before and 48 hours after the traumatic event, or 24 hours before and 72 hours after the traumatic event. In all cases, concomitant administration can be extended for 4, 5, 6, 7, 8, 9, 10, 11, 12, 13, 14, 15, 16, 17 or 18 weeks to achieve more efficient protection.

The first object of the present invention is therefore to provide a method for treating patients suffering from anxiety disorders, whether or not associated with depression, by administering in particular a compound of formula (I) or a pharmaceutically acceptable salt of formula (II). In particular, the method does not induce a schizophrenia-inducing effect.

The present invention has as its object the use of a compound of formula (I) or a pharmaceutically acceptable salt of formula (II), in the manufacture of a medicament for the treatment of anxiety disorders, whether or not associated with depression.

As described in the following examples, the anxiolytic and possibly antidepressant activity of compounds of formula (I) can be assessed using appropriate animal paradigms.

Thus, thanks to the experimental paradigm of the light-dark box, the applicant discovered that the compounds of formula (I) or (II) according to the present invention have significant anxiolytic properties and this from the first injection for a dosage of 10 mg/kg, contrary to memantine which induces an increased time of presence in the dark compartment. For comparison, a molecule such as fluoxetine has such anxiolytic activity for doses of 5 mg/kg but only after 7 days of treatment.

This discovery was verified by the implementation of the open-field test in the presence of light gradients. Under these conditions, the compound according to the invention significantly limits the avoidance of the brightest area of the field by the rodent during the exposure phase, or even cancels it out completely, in particular at the 10 mg/kg dose.

Similarly, through the forced swimming test, the applicant discovered that the compound according to the present invention induces a significant decrease in the immobility time in rats as when they are treated with memantine or ketamine, which reflects an antidepressant behavior of these molecules and compounds.

The applicant also confirmed this surprising advantage of a compound according to the invention in the treatment of anxiety disorders, whether or not associated with depression, by using them in a fear conditioning test with an extinction and stabilization phase. This paradigm, commonly used to test the effectiveness of PTSD treatments, has shown that a compound according to the present invention, in a surprising manner, makes it possible, in particular at doses of 10 mg/kg and 20 mg/kg, to protect the patient against the persistence of the disorders during the stabilization phase, and this more particularly when the compound is administered concomitantly with the conditioning phase. In the same test, no effects were observed or for propranolol. The effects observed for FENM are equivalent to or greater than those observed by C. Denny for ketamine injected in much larger amounts one week prior to conditioning. Still surprisingly, the applicant noted that a similar beneficial effect in intensity, and more particularly for the same doses, could be observed when the compound according to the invention was administered before the stabilization phase, i.e. during a consolidated PTSD syndrome. In the same test, no effect was observed or for propranolol.

The compounds according to the invention are, finally, also effective for the elimination of persistent disorders, particularly when they are administered during the extinction phase, more particularly at a dose of 20 mg/kg. In this test, propranolol reduces tetany during the extinction phase but this beneficial effect is lost during the stabilization phase.

It should also be noted that a significant rebound effect is observed during the stabilization phase for memantine when administered during the extinction phase. This effect, in addition to demonstrating different mechanisms of action for memantine and FENM, is consistent with the clinically observed ineffectiveness of memantine in the treatment of PTSD.

Furthermore, the applicant observed that when the beneficial effects of a compound according to the invention were found, no inhibition effect of the pre-impulse effect was registered, whereas memantine produces an inhibition effect. This absence of schizophrenia-inducing effect is very favorable to the development of a new treatment for anxiety, whether or not associated with depression, insofar as this schizophrenia-inducing effect is observed for most of the molecules proposed elsewhere (including benzodiazepines in general and diazepam in particular, as well as ketamine).

The compound according to the invention can be administered in various ways in order to obtain anxiolytic or antidepressant effects. The compound according to the invention can be administered alone or in the form of pharmaceutical preparations, to the patient to be treated, either orally or parenterally (subcutaneously or intravenously, etc.).

The amount of compound administered can vary and can be any amount responsible for anxiolytic and/or antidepressant effects. Depending on the patient and the method of administration, the amount of compound administered can vary over a wide range from 0.01 mg/kg to 20 mg/kg, preferably between 0.05 mg/kg and 15 mg/kg of patient weight per dose.

The unit doses of the compound according to the invention can contain, for example, from 5 mg to 1000 mg, preferably from 5 to 30 mg, and can be administered, for example, from 1 to 4 times a day.

The present invention relates to the use of a medicinal product formulated from the compound according to the invention in association with a pharmaceutical or cognitive-behavioral therapeutic method for the treatment of anxiety disorders, whether or not associated with depression.

For the purposes of the present invention, "cognitive-behavioral therapy", or CBT, means cognitive-behavioral psychotherapies, which includes a set of treatments for psychiatric disorders (in particular addictions, psychoses, depression and anxiety disorders) that share an approach according to which the therapy is based on knowledge derived from scientific psychology. It follows relatively standardized protocols. It often evaluates the patient's progress during therapy. It accepts the approach of evidence-based medicine. The particularity of CBTs is that they address the patient's difficulties in the "here and now" through practical exercises centered on the symptoms observable through behavior and through the accompaniment by the therapist who aims to intervene on the mental processes also known as cognitive processes, conscious or not, considered as the origin of emotions and their disorders. The standardization of the practice of CBTs has contributed to the recognition of their effectiveness through their reproducible nature, which is one of the requirements of the scientific approach. They are particularly indicated for anxiety disorders (especially phobias) and addictions.

In particular, the applicant proposes to implement a combination of the prophylactic administration of ketamine and a drug containing a compound according to the invention after traumatic exposure, in order to treat PTSD. Similarly, the applicant proposes to implement a combination of the administration of propranolol combined with cognitive therapy during an initial treatment period for PTSD and treatment with a medicinal product containing the compound according to the invention during the withdrawal phase, in order to treat the anxiety disorders present in patients who have suffered abuse, in particular during childhood.

EXAMPLES

Animal Models

The development of drugs to treat a disease often involves the use of animal models to test their efficacy and toxicity before testing them in humans.

Animal models are considered valid when they meet the following three criteria: predictive validity, symptom isomorphism and construct validity. Of course, the results from these animal models should not depend on the experimenters and the use of automated conditioning and observation means is increasingly developed (use of photoelectric cells, video tracking, etc.).

Use of Animal Models for Anxiety

In the field of anxiety, animal models have been used for many years and have been improved as new observation techniques have been developed and as biases in their validity have been observed (see, for example, the course by M Roy "Animal models of anxiety disorders" available online at http://psychobiologierouen.free.fr/?page_id=40). Most animal models are developed with rodents.

In the case of anxiety, several animal models make it possible to induce and measure it by subjecting them to situations of danger either by simple exposure to the novelty or by subjecting them to a previously reinforced situation. These animal models have been validated in particular by verifying their predictive character of the response in humans.

Thus, to test state anxiety, several animal models are commonly used and have been validated by numerous studies:
  open field test: This consists of forcibly exposing the animal (rat or mouse) to a new environment and observing its behavior. The animal is usually placed in a cage or box with a grid floor that it does not know. Locomotor activity and behavior are then assessed by recording the number of crossings of the grid lines, the frequency of retreats, the number of entries and the time spent in the central squares. This animal model is considered a good model of "normal" anxiety when adapting to a new environment. It has good predictability of human response to treatment (L. Prut, European Journal of Pharmacology 463 (2003) 3-33). The open-field test is also useful, when it is prolonged (behavioral recording time over 2 hours), as it allows monitoring the motor activity of the animals and thus their state of wakefulness, whereas measurements at short times give information on anxiety.
  the light-dark box test: another animal model of anxiety is based on the aversive properties of an open-field space and on the comparison of exploratory activities in a lit compartment and in a dark compartment under the influence of anxiolytic substances (M Bourin, European Journal of Pharmacology 463 (2003) 55-65). This paradigm is based on rodents' innate aversion to bright places and on rodents' spontaneous exploratory behavior in response to stressful environments (new environment or light). The test device is divided into two compartments, one is small, dark and safe, the second is large, bright and stressful. This paradigm allows the prediction of anxiolytic or anxiogenic drug-like activities in mice. Passages between each compartment are a cue of exploration activity, while the time spent in each compartment reflects aversion. Anxiolytics, effective in humans, classic (benzodiazepines) as well as more recent anxiolytic compounds (serotonergic drugs or drugs acting on neuropeptide receptors) can be detected by this animal model which has the advantage of being simple and quick to use.
  The open-field test with light gradient: the two models described above can be judiciously coupled in order to check the anxiolytic potential of a molecule, by eliminating the "burrow" effect induced by the presence of the dark compartment.

Use of Animal Models for Depression the forced swimming test: This test has been used for a number of years with rats or mice to test the activity of antidepressants (F. Borsini, Psychopharmacology (1988) 94:147-160) and consists of placing the animal in a bowl filled with room-temperature water. After 15 minutes (pre-test session), the animal is taken out of the water and dried. Twenty-four hours later, the animal is again exposed to the previous conditions and the time of total immobility for a period of 5 minutes is recorded (test session). The animal is considered immobile when it performs only the movements necessary to keep its head out of the water. This immobility is easier to assess in rats than in mice, which have less explicit movements.

Initially, the fact that the animal was more immobile during the second immersion appeared to be an indicator that the animal had learned that it could not escape during the pre-test. This immobility therefore seemed to be an indication of a certain "desperation" on the part of the animal. Although this interpretation is now more nuanced, as it is possible to explain this increased immobility by other reasons (response adapted to a situation already known, etc.), this test remains one of the leading paradigms of depression and gives very good results of the antidepressant activities of the drugs.

Use of Animal Models for PTSD

Many research groups (for example Pier-Vincenzo Piazza and Aline Desmedt from INSERM) have shown that the memory difficulties associated with PTSD are not specific to humans and are found in rodents (see for example Kaouane N. Science 335, 1510 (2012). Animal models are therefore regularly used to understand the mechanisms of the onset of PTSD (Zovkic, Neuropsychopharmacology REVIEWS (2013) 38, 77-93) or to test potential treatments for PTSD (for example in patent JP2007148435).

Several animal models have been developed to mimic the traumatic events that induce intense and recurrent fear symptoms characteristic of PTSD.

Pavlovian fear conditioning of the animals: This animal model consists of Pavlovian-type fear conditioning (Zovkic, Neuropsychopharmacology Reviews (2013) 38, 77-93): mice (or rats) are trained to associate exposure to danger (electric shock, etc.) with the presence of a specific cue or environment (sound cue for example). The memory of this association (danger-cue) is later tested by measuring tetany behavior (through fear) when the animal is re-exposed to the conditioning cue in the absence of real danger.

Fear conditioning has many advantages as a model of PTSD. First of all, rodents, like patients with PTSD, are subjected to a traumatic event and the memory of this event persists over a long period of time. Second, the re-experiences of the traumatic event or typical avoidances of PTSD can be modeled by exposing the rodent to the sound cue or context associated with the hazard, without requiring actual re-exposure to the traumatic event itself (electric shock). In addition, the hyperactivity of the nervous system observed in patients with PTSD can be assessed by comparing the amplitude and onset of bursts produced in response to a sound reminiscent of the trauma. Finally, studies on PTSD have shown that the brain regions involved include the amygdala, hippocampus and prefrontal cortex, which are also involved in fear conditioning in animals.

Thanks to this animal model, it is therefore possible to test the influence of different experimental variables, or different treatments on the pathological memory of fear, by simply observing whether they increase, decrease or suppress tetany behavior. The severity of the traumatic event can therefore be increased or decreased by decreasing the intensity of the electric shock and attempting to link it to the persistence and strength of the memory of this fear.

Other animal models are also commonly used as PTSD paradigms, such as exposure to one or more predators, with varying degrees of contact (exposure to smell, to the animal itself, etc.).

Again, the occurrence of symptoms of PTSD are assessed after a certain period of time, without exposure to the hazard, to simulate the long-term onset of PTSD pathology.

Fear extinction: After a fear conditioning as described above it can be of interest to apply a protocol to extinguish this fear. Classically, this phase is placed 24 hours after the conditioning phase.

To do this, the conditioned animal is trained so that the conditioning cue (sound) no longer predicts the occurrence of danger (electric shock).

Although extinction can appear as the cancellation of learning to the previous fear, it is not equivalent to an erasure of memory or a definitive forgetting, since, on the one hand, tetany is not completely eliminated by the extinction phase and, on the other hand, the response to the stimulus can reappear spontaneously or following a shock. The extinction protocols model the relearning of the normal (non-fear-motivated) response to the cue (sound) and are very useful in modeling PTSD.

Fear stabilization: It can be useful, to assess the performance of a treatment, to add a stabilization phase after the extinction phase, spaced 24 h apart. Typically, this phase puts the animals back under the extinction phase conditions. It then allows the detection of staggered performances of the treatments, but also of the resurgence of tetany (rebound effect).

It also allows us to model a "consolidated" PTSD, i.e. the situation where an individual exposed to a psychological trauma (one-time or prolonged) and treated (or not) by conventional methods, presents the residual disorders of this trauma.

Use of Animal Models for the Development of Schizophrenic Disorders

Pre-pulse inhibition (PPI) test: One of the major problems of treatments targeting the central nervous system remains the achievement of the desired effect without the appearance of crippling psychological side effects, even exceeding the therapeutic benefit of the treatment. These effects are often significant (the rebound effect of benzodiazepines) or even paradoxical (the anxiety-producing effect of short-term serotonin reuptake inhibitors). In particular, they can induce a destabilization of sensory filtering and generate symptoms similar to schizophrenia.

Pre-impulse inhibition testing is based on the brain's ability to adapt to a moderate-intensity stimulus in order to limit the effect of the same high-intensity stimulus. In this test, the animals are placed in a soundproof cage and subjected either to a sound pulse of 120 decibels (dB) or to a sequence of 2 pulses spaced about 100 milliseconds apart, the second pulse being of fixed intensity of 120 dB and the first of variable intensity between 70 and 85 dB).

In a normal animal, the first sound impulse has the ability to partially inhibit the startle caused by the loudest sound. In animals with psychotic disorders of a schizophrenic nature, this inhibition is more or less eliminated.

The PPI test in rodents is a powerful test insofar as it is reproducible in humans in whom it can detect schizophrenic disorders, as well as the adverse effect of pharmaceutical treatments (PCP, benzodiazepine, ketamine).

In the following examples, the effects of memantine, propranolol and fluoroethylnormemantine (FENM, the subject of the present invention) are studied in naive rats (Wistar) subjected to various tests related to depression or anxiety and then compared.

The test substances are administered to rats intraperitoneally in a volume of 5 ml/kg, 30 minutes before the behavioral tests are performed.

The injected solutions contain either of the molecules in the form of one of their salts, a hydrochloride (memantine·HCl and FENM·HCl) for the nitrogen derivatives and as such for propranolol, at the concentrations indicated below in a mixture of 95% (NaCl 0.9% ww in water)/5% ethanol. In each experiment, the dose per kilogram is referenced.

In this way, the animals are given a constant volume of solution (to the nearest difference in weight) equal to 5 ml/kg, or 1.5 ml for a 300 g rat.

For each paradigm, and each solution tested, 12 rats are subjected to injection and behavioral testing. The control solution is a saline solution.

Example 1: Anxiety Treatment and Locomotor Activity

Open-field test: The locomotor activity of the animals and the "normal" anxiety associated with the discovery of an unknown environment are measured in an open field using a video monitoring system for 2 hours, 30 minutes after the injection of the solutions to be tested. The recorded data include, with a reading every 5 minutes, the time spent in the central squares, vertical activity, and the number of displacements.

Tables 1 to 3, below, report the effects of FENM.HCl, comparing memantine and a control saline solution.

TABLE 1

| | Mean time spent in the central squares per time interval (s) | | | |
|---|---|---|---|---|
| Animal group | 0-5 min | 5-10 min | 0-10 min | 0-120 min |
| Control | 132.9 | 104.9 | 237.8 | 2293.4 |
| Memantine 10 mg/kg | 90.4 | 46.3 | 136.8 | 1874.8 |
| FENM 5 mg/kg | 128.8 | 88.0 | 216.8 | 1563.6 |
| FENM 10 mg/kg | 116.8 | 109.9 | 226.7 | 1803.8 |
| FENM 20 mg/kg | 129.8 | 105.9 | 235.7 | 1692.8 |

TABLE 2

| | Vertical activity | | | |
|---|---|---|---|---|
| Animal group | 0-5 min | 5-10 min | 0-10 min | 0-120 min |
| Control | 49.83 | 26.58 | 76.42 | 115.33 |
| Memantine 10 mg/kg | 11.33 | 4.67 | 16.00 | 60.08 |
| FENM 5 mg/kg | 40.67 | 30.50 | 71.17 | 136.00 |
| FENM 10 mg/kg | 52.33 | 34.08 | 86.42 | 173.75 |
| FENM 20 mg/kg | 47.33 | 19.25 | 66.58 | 208.92 |

TABLE 3

| Animal group | Number of displacements 0-120 min |
|---|---|
| Control | 1650 |
| Memantine 10 mg/kg | 750 |
| FENM 5 mg/kg | 1600 |
| FENM 10 mg/kg | 1800 |
| FENM 20 mg/kg | 2100 |

The results of the various measurements show that FENM.HCl, even at high doses, does not generate the drowsiness effect observed for memantine which decreases the overall activity level of the animals, without improving the time of presence in the center of the field. This effect is particularly noticeable over the 2-hour long duration of the experiment.

Example 2: Anxiety Treatment (Light-Dark Box Paradigm)

In this example the light-dark box test was used. As it is based on rodents' innate aversion to light, the increase in time spent in the lighted compartment is therefore considered to reflect a lower level of anxiety.

The box used for this test is divided into a white behavior with high-power illumination (600 lux) and a black behavior with a lid (about 5 lux). The number of entries and the time spent in the illuminated compartment (anxiety zone) are recorded for 10 minutes by a video monitoring system. In addition, the system makes it possible to differentiate the periods between 0 and 5 minutes and between 5 and 10 minutes.

Table 4 below shows the presence times in the lighted compartment for different doses of FENM·HCl, comparing memantine and a control saline solution.

TABLE 4

| | Time spent in the lighted compartment (s) | | |
|---|---|---|---|
| Animal group | 0-5 min | 5-10 min | 0-10 min |
| Control | 34.1 | 37.0 | 71.1 |
| Memantine 1 mg/kg | 34.2 | 25.7 | 59.9 |
| Memantine 3 mg/kg | 26.2 | 8.1 | 34.3 |
| Memantine 10 mg/kg | 31.0 | 0.9 | 32.0 |
| FENM 1 mg/kg | 42.4 | 28.6 | 71.0 |
| FENM 3 mg/kg | 34.4 | 33.2 | 67.5 |
| FENM 10 mg/kg | 96.8 | 75.0 | 171.9 |

The results show a large and significant increase (Student's t-test $p<0.01$) in the time spent in the lighted compartment of the box for animals treated with the 10 mg/kg FENM solution, compared with the control, while no effect was observed for memantine. This result demonstrates the anxiolytic effect of the compound according to the invention and a different mode of action and effect compared with memantine.

This indeed demonstrates that memantine has no anxiolytic effect.

Example 3: Treatment of Anxiety (Light-Gradient Field Paradigm)

In this example the light-dark box test was modified by eliminating the compartmentalization of the box and using a high-intensity light gradient (600 lux). As it is based on rodents' innate aversion to light, the increase in time spent in the area closest to the light source is therefore considered to reflect a lower level of anxiety.

The animals are exposed to a 12-minute sequence, broken down into three parts, 4 minutes in darkness (ambient light of 5 lux), 4 minutes in the presence of the light gradient and 4 minutes again in darkness. Displacements are recorded in the same way as for the open-field test. The field of view is divided into 4 zones numbered from 1 to 4 according to the increasing distance from the light source.

Table 5 below shows the effects of different doses of FENM·HCl compared with the control solution.

TABLE 5

| | Percentage of time spent in the area closest to the light source | | |
|---|---|---|---|
| Animal group | Dark 1 (Habituation) | Light 600 lux (Stress) | Dark 2 (Relief) |
| Control | 32% | 15% | 30% |
| FENM 5 mg/kg | 32% | 22% | 30% |
| FENM 10 mg/kg | 29% | 30% | 34% |
| FENM 20 mg/kg | 39% | 21% | 29% |

The results show, for animals treated with FENM·HCl, a significant reduction in avoidance by animals in the most strongly illuminated area, signifying a net decrease in anxiety. In the case of the 10 mg/kg dose, the anxiety effect is completely eliminated and the animals spend the same amount of time in the area close to the source, in the presence and absence of light.

Moreover, this effect of cancelling or reducing anxiety is found to have no other known effect on the behavior of the animals and, in particular, on their ability to move around.

Example 4: Treatment of Depression (Forced Swimming)

In the forced swimming test, rats (12 per group) are forced to swim in a tank filled with 23° C. water (10 minutes on the first day to allow for habituation to the medium and 6 minutes on the second day).

The behavior of the rats (stopping swimming, decreasing activity) is quantified by a video monitoring system.

The therapeutic solutions to be tested are administered on the second day 30 minutes before the experiment. Resigned animals are those that will exhibit (a) a longer immobility time and (b) spend less time trying energetically (frantically) to get out of the beaker, i.e. "depressive" type behavior.

Table 6 below reports the effects observed on these two parameters at different doses of FENM·HCl compared with memantine and a control saline solution.

TABLE 6

| Animal group | Rat behavior over the period of time 1 to 6 minutes | |
|---|---|---|
| | immobility (ies) | frenetic movement (s) |
| Control | 177.5 | 35.6 |
| Memantine 1 mg/kg | 139.8 | 55.1 |
| Memantine 3 mg/kg | 145.7 | 48.7 |
| Memantine 10 mg/kg | 119.7 | 67.2 |
| FENM 1 mg/kg | 157.8 | 43.2 |
| FENM 3 mg/kg | 164.3 | 47.6 |
| FENM 10 mg/kg | 140.5 | 60.6 |

The results show a very significant ($p<0.001$) decrease in immobility time and a significant increase in frenzy effects, demonstrating comparable antidepressant effects for memantine and the compound according to the invention (FENM). This effect is observed at all dose levels and is particularly noticeable at 10 mg/kg.

Example 5: Treatment of PTSD (Fear Conditioning+Extinction+Stabilization)

Extinction protocols that model the relearning of the normal (non-fear-motivated) response to the cue (sound) are very useful in modeling PTSD.

The applicant used a fear conditioning test in which the clue (neutral conditional stimulus) is a sound, coupled with a danger (aversive unconditional stimulus) which is an electric shock delivered by the floor of the box. This conditioning is followed by a fear extinction phase with injection of the treatment solutions to be tested and then by a test phase itself.

Fear Conditioning Phase (FC): fear conditioning takes place in a standard conditioning box (context A, white box in Table 7) and the rats (8 per group) are subjected to 3 "sound-electroshock" pairs at times of 180 s, 381 s and 582 s after being placed in the box. Each sound lasts 20 s and each electroshock lasts 1 s with a current of 1 mA.

The fear extinction phase (Ext.) is conducted as follows: the rats are placed in a box similar to the one that will be used for the final test (context B, pink box in Table 7), for a 25-minute session. During this session, 24 presentations are made with the same sound as that used during the conditioning session (20 s each, 35 s apart). Of course, no electric shock is delivered, and the percentage of time of tetany ("freezing") during the phase is recorded.

Stabilization phase: the day after the extinction phase, 30 minutes before the test phase, the rats are injected with saline and then tested for fear response in context B by subjecting them to a sequence of 3 sounds (same sequence as used for conditioning), recording the percentage of time they remain still during this test phase.

Table 8 below reports the effects on the percentage of time the animals were immobile during the stabilization phase for different doses of FENM·HCl compared with propranolol and a control saline solution under three treatment conditions:

Protective effect—one injection 30 minutes before the conditioning phase

Early treatment—one injection 30 minutes before the extinction phase

Late treatment—one injection 30 minutes before the stabilization phase

TABLE 8

| Animal group | Percentage of time of tetany (freezing) during the stabilization phase | | |
|---|---|---|---|
| | Protective effect | Early treatment | Late treatment |
| Control | 37% | 33% | 28% |
| Propranolol 10 mg/kg | 28% | 26% | 29% |
| FENM 5 mg/kg | 23% | 21% | 26% |
| FENM 10 mg/kg | 6% | 25% | 4% |
| FENM 20 mg/kg | 2% | 6% | 2% |

These results show that FENM has the potential to virtually eliminate ($p<0.001$) the phenomenon of tetany in the stabilization phase, both when administered at the time of conditioning and during early or late post-traumatic treatment. Propranolol does not differentiate from the control in the stabilization phase while improving the extinction phenomenon, which is consistent with published data in the literature on post-weaning rebound.

It should also be noted that a significant rebound effect (increased tetany) is observed (+25% compared with control) during the stabilization phase when memantine is administered at 10 mg/kg during the extinction phase.

Example 6: Lack of Disturbance of "Sensory Filtering" (PPI Test)

Pre-impulse inhibition testing is based on the brain's ability to adapt to a moderate-intensity stimulus in order to limit the effect of the same high-intensity stimulus. In this test, the animals (12 per group) are placed in a soundproof cage and subjected either to a sound pulse of 120 decibels (dB) or to a sequence of 2 pulses spaced about 100 milliseconds apart, the second pulse being of a fixed intensity of 120 dB and the first of variable intensity between 70 and 85 dB).

In a normal animal, the first sound impulse has the ability to partially inhibit the startle caused by the loudest sound. In animals with psychotic disorders of a schizophrenic nature, this inhibition is more or less eliminated.

Table 9 below reports the effects observed on these two parameters in the presence of different doses of FENM·HCl, compared with memantine or a control saline solution.

TABLE 9

| Animal group | Percentage of pre-pulse inhibition as a function of the intensity of the first pulse | | | | |
|---|---|---|---|---|---|
| | 72 dB | 76 dB | 80 dB | 84 dB | Average |
| Control | 38% | 46% | 54% | 66% | 51% |
| Memantine 10 mg/kg | 19% | 24% | 36% | 44% | 31% |
| FENM 5 mg/kg | 24% | 37% | 47% | 60% | 42% |
| FENM 10 mg/kg | 27% | 39% | 51% | 64% | 45% |
| FENM 20 mg/kg | 31% | 46% | 54% | 62% | 48% |

These results show that, while memantine at 10 mg/kg induces an inhibition of the PPI effect (p<0.01, an effect comparable to the effects reported in the literature for this compound), FENM induces no effect, even at high dose (20 mg/kg). This means that memantine has the undesirable effect of causing schizophrenia, whereas FENM does not have the undesirable effect of causing schizophrenia.

In this test, the performance of memantine, and implicitly, the lack of performance of FENM, demonstrates a schizophrenic side effect of this memantine. This effect is particularly undesirable. Indeed, it is undesirable because not only is this type of behavior a source of suffering for the patient but, moreover, it generates anxiety-provoking stress which will increase anxiety rather than decrease it.

The invention claimed is:

1. A method comprising treating an anxiety disorder in a patient in need thereof via administration to the patient of a compound of formula (I) or a pharmaceutically acceptable salt thereof

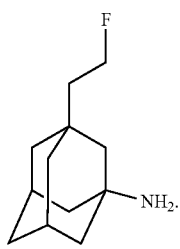

(I)

2. The method according to claim 1, wherein the pharmaceutically acceptable salt corresponds to formula (II)

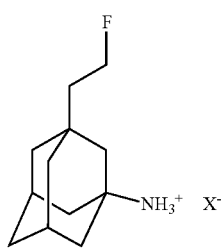

(II)

wherein $X^{31}$ denotes a counter-anion selected from the group consisting of chloride, bromide, iodide, acetate, methane sulfonate, benzene sulfonate, camphosulfonate, tartrate, dibenzoate, ascorbate, fumarate, citrate, phosphate, salicylate, oxalate, bromohydrate and tosylate ions.

3. The method according to claim 1, wherein the anxiety disorder is associated with depression.

4. The method according to claim 1, wherein the anxiety disorder is associated with insomnia.

5. The method according to claim 1, wherein the anxiety disorder is selected from the group consisting of post-traumatic stress disorder (PTSD), specific phobia, social phobia, generalized anxiety disorder, panic disorder with or without agoraphobia, and obsessive compulsive disorder.

6. A method comprising prophylactically treating a patient in need thereof via administration to the patient of a compound of formula (I) or a pharmaceutically acceptable salt thereof, to thereby prevent the appearance in the patient of anxiety disorders related to post-traumatic stress

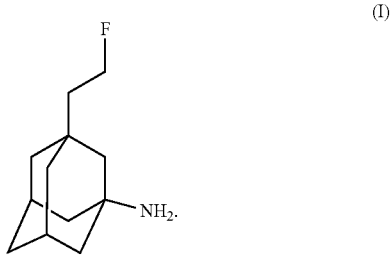 [SMILES: NC12CC3CC(C1)CC(CCF)(C3)C2]

(I)

7. The method according to claim 1, wherein the anxiety disorder is related to established post-traumatic stress.

8. The method according to claim 1, wherein the anxiety disorder is accompanied by acute anxiety attacks and episodes.

9. The method according to claim 1, comprising administering to the patient a combination product that comprises:
component (A) comprising said compound of formula (I) or said pharmaceutically acceptable salt thereof, and
component (B) comprising propranolol,
wherein each of said components (A) and (B) is formulated with at least one pharmaceutically acceptable excipient.

10. The method according to claim 9, said patient having suffered repeated abuse during childhood.

11. The method according to claim 1, comprising administering to the patient a combination product that comprises:
component (A) comprising said compound of formula (I) or said pharmaceutically acceptable salt thereof, and
component (C) comprising an antidepressant;
wherein each of said components (A) and (C) is formulated with at least one pharmaceutically acceptable excipient .

12. The method according to claim 9, comprising separately administering to the patient said compounds (A) and (B), said patient having suffered repeated abuse during childhood.

* * * * *